United States Patent [19]

Dougherty et al.

[11] Patent Number: 5,137,448

[45] Date of Patent: * Aug. 11, 1992

[54] DENTAL IMPRESSION METHOD WITH PHOTOCURING OF IMPRESSION MATERIAL IN LIGHT TRANSMISSIVE TRAY

[75] Inventors: Emery W. Dougherty, York, Pa.; Wu-Lan Wang, Milford, Del.

[73] Assignee: Dentsply Research & Development Corp., Milford, Del.

[*] Notice: The portion of the term of this patent subsequent to Nov. 19, 2002 has been disclaimed.

[21] Appl. No.: 649,188

[22] Filed: Feb. 4, 1991

Related U.S. Application Data

[60] Continuation of Ser. No. 177,819, Apr. 8, 1988, abandoned, which is a division of Ser. No. 881,473, Jun. 30, 1986, abandoned, which is a continuation of Ser. No. 636,138, Jul. 31, 1984, abandoned.

[51] Int. Cl.$^5$ ............... A61C 9/00; C08F 230/08; C08F 2/50
[52] U.S. Cl. .................... 433/214; 433/37; 264/22; 264/222; 522/24; 522/28; 522/90; 522/99; 526/279; 528/32
[58] Field of Search ............................ 433/37, 214

[56] References Cited

U.S. PATENT DOCUMENTS

| | | | |
|---|---|---|---|
| 1,084,017 | 1/1914 | Lautenberg | 433/37 |
| 3,453,242 | 7/1969 | Schmitt et al. | 260/77.5 |
| 3,629,310 | 12/1971 | Bailey et al. | 260/448.8 |
| 3,792,073 | 2/1974 | Prokai et al. | 260/448.8 |
| 3,816,282 | 6/1974 | Viventi | 522/99 |
| 3,821,325 | 6/1974 | Merritt, Jr. et al. | 260/824 |
| 3,836,560 | 9/1974 | Prokai et al. | 260/448.8 |
| 3,867,420 | 2/1975 | Morehouse et al. | 260/448.2 |
| 3,874,376 | 4/1975 | Dart et al. | 128/90 |
| 3,887,601 | 6/1975 | Kanner et al. | 260/448.2 |
| 3,950,300 | 4/1976 | Hittmair et al. | 260/37 |
| 3,998,979 | 12/1976 | Armstrong et al. | 427/54 |
| 4,064,027 | 12/1977 | Gant | 522/99 |
| 4,070,526 | 1/1978 | Colquhoun et al. | 428/537 |
| 4,110,184 | 8/1978 | Dart et al. | 522/14 |
| 4,116,786 | 9/1978 | Hodakowski | 522/91 |
| 4,130,708 | 12/1978 | Friedlander et al. | 528/28 |
| 4,182,829 | 1/1980 | Walkowiak et al. | 528/75 |
| 4,201,808 | 5/1980 | Cully et al. | 428/40 |
| 4,218,294 | 8/1980 | Brack | 525/533 |
| 4,259,467 | 3/1981 | Keogh et al. | 526/279 |
| 4,276,402 | 6/1981 | Chromecek et al. | 526/264 |
| 4,290,869 | 9/1981 | Pigeon | 528/447 |
| 4,306,042 | 12/1987 | Neefe | 526/75 |
| 4,348,454 | 9/1982 | Eckberg | 522/99 |
| 4,359,369 | 11/1982 | Takamizawa et al. | 430/288 |
| 4,449,928 | 5/1984 | von Weissenfluh | 433/229 |
| 4,468,202 | 8/1984 | Cohen | 433/199 |
| 4,528,081 | 7/1985 | Lien et al. | 522/99 |
| 4,543,398 | 9/1985 | Bany et al. | 522/99 |
| 4,553,936 | 11/1985 | Wang | 433/37 |
| 4,554,339 | 11/1985 | Hockemeyer et al. | 528/26 |
| 4,585,670 | 4/1986 | Liu | 522/99 |
| 4,597,987 | 7/1986 | Hockemeyer et al. | 427/54.1 |
| 4,659,786 | 4/1987 | Kawakani et al. | 525/415 |

FOREIGN PATENT DOCUMENTS

| | | |
|---|---|---|
| 0097333 | 1/1984 | European Pat. Off. |
| 0174713 | 3/1986 | European Pat. Off. |
| 2226154 | 11/1974 | France |

OTHER PUBLICATIONS

Dow Corning—New Product Information letter, Organofunctional Silicone Fluids—Silicone Polycarbinols—dated Feb. 1, 1975.

Jet Propulsion Laboratory—Technical Support Pckage on Silicone/Acrylate Copolymers, May, 1982, NASA Tech Brief, vol. 6, No. 3, Item 24, from JPL Invention Report SC 1227/NPO-15523.

Primary Examiner—Marion E. McCamish
Assistant Examiner—Arthur H. Koeckert
Attorney, Agent, or Firm—Edward J. Hanson, Jr.

[57] ABSTRACT

Disclosed in the present application is a method of curing a dental impression material by passing actinic light through a tray while the tray is in contact with the impression making composition, a new dental impression composition that is polymerizable by having an initiator activated by actinic light within the visible light range of 360 to 600 nanometers, a new composition of matter that is a compound having at least two terminal acrylate unsaturations and an organosilicone containing backbone and a new method of forming dental prosthetics by directly forming against the soft tissue of the oral cavity and then setting with visible light curing.

13 Claims, No Drawings

DENTAL IMPRESSION METHOD WITH PHOTOCURING OF IMPRESSION MATERIAL IN LIGHT TRANSMISSIVE TRAY

This is a continuation of application Ser. No. 177,819, filed Apr. 8, 1988 abandoned, which is a divisional of application Ser. No. 881,473 filed Jun. 30, 1986, abandoned, which is a continuation of Ser. No. 636,138 filed Jul. 31, 1984, abandoned.

BACKGROUND OF THE INVENTION

This invention relates to a method of forming a dental impression and dental impression materials which quickly take a set accurately conforming to dental surfaces to be recorded and also to a method of preparing a dental prosthetic by direct conforming of a dental material to the surfaces of the oral cavity and then curing the dental material with visible light.

Methods of forming dental impressions are well known as are dental impression materials that are capable of accurately reproducing the surface contours and dimensions of oral tissues required in preparing dental prostheses. Since anatomic structures and preparations for prosthetic appliances are usually undercut, preferred impression materials are elastic or rubbery, ranging from gels, such as agar or algin preparations, to elastomers, such as rubbers, silicones, and polyethers. The nonaqueous elastomers are preferred because of their extreme dimensional accuracy and their relative stability under ambient conditions. In spite of all the improvements which have characterized current dental impression materials, they are still greatly limited by clinical factors when they are used in vivo.

It is known to prepare elastomeric impression materials by taking two separate pastes (one containing a catalyst and the other containing an accelerator), placing measured amounts of each on a pad of parchment or polyethylene-coated paper and immediately mixing them with a spatula into a substantially homogeneous mass. Such impression materials must be used immediately after mixing and while curing to set is rapid, it must be timed to allow placement by fast and slow dental practitioners and because the curing time is built in, special problems cannot be controlled with any degree of accuracy by the dental practitioner. All parts of the impression polymerize at substantially the same time. Also, the act of mixing tends to introduce air bubbles into the viscous pastes and these bubbles are difficult to eliminate, tending to cause surface imperfections in the finished impression or to distort the impression. Mixing is inconvenient and a source of inconsistency.

In the usual practice, a dental practitioner places the mixed paste in juxtaposition to the dental tissues, using either a supporting tray to contain the paste or a combination of a placement syringe and a supporting tray. The dental practitioner or dentist and the patient then wait, sometimes for ten minutes, for the polymerization reaction to progress to completion and the material to become sufficiently elastic so that the impression may be removed from the tissue without distortion of the remembered shape or form. The rate of faulty impressions is quite high due to the patient's natural tendency to move during this time, and a gagging reflex is common. The dental practitioner loses valuable time while he is thus inactivated, plus time needed for the often required retakes.

Materials commonly used for taking impressions are polysiloxanes such as described in U.S. Pat. No. 3,950,300, polyethers such as described in U.S. Pat. No. 3,453,242, and other elastomeric materials having properties more fully described in American Dental Association Specification 19.

SUMMARY OF THE INVENTION

The present invention has important independently claimed aspects. The first claimed aspect's central feature is curing a dental impression material by passing actinic light through a tray while the tray is in contact with the impression making composition. A second claimed aspect is a new dental impression composition that is a polymerizable composition that has as a central feature having an initiator activated by actinic light within the visible light range of 360 to 600 nanometers. A third claimed aspect is a new composition of matter that is a compound having as a central feature a characteristic of having at least two terminal acrylate unsaturations and an organosilicone containing backbone. Yet another independently claimed aspect of the present invention is the provision of a new denture reline method and material. Many other preferred attributes are claimed but are important enhancements to the above recited aspects.

DESCRIPTION OF THE PREFERRED EMBODIMENT

The present invention in a preferred embodiment of one of its aspects is a method of forming a dental impression in the oral cavity. First, the surfaces to be taken are cleaned and cleared of anything on them including mouth fluids. Then a composition that is flowable, at least substantially free of memory and capable of assuming a permanent elastomeric memory in response to contact by actinic light is engaged with the surfaces that are to have their dental impression made. This includes in a preferred embodiment, forcing a tray of the composition toward the surface until some of the composition flows to assure a good engagement of the composition with the surfaces to be recorded. The tray is preferably maintained in contact with the composition to hold it securely in place, and actinic light is passed through at least an integral part of the tray activating the photopolymerizing of the composition to a degree that the composition assumes a permanent elastic remembered form.

A preferred tray passes actinic light through all of its mass to the composition. For this purpose, the tray may be a clear plastic.

In the aspect of the present invention involving the actinic light activated photopolymerizing composition, the composition is for health and safety reasons preferably one that can be expeditiously cured using light filtered to limit the wave lengths to the visible light range of approximately 360–600 nanometer More preferably the curing is carried out with the greater portion of the light being within the 400–500 nanometer range.

In its preferred form, the method includes aspects of the materials that can perform the needed actions for preferred performance of the preferred methods of the present invention. The preferred method does not require pre-mixing of the composition before its use. The preferred compositions are one-component mixtures of monomeric, oligomeric and/or polymeric elastomer forming materials of high or low molecular weight and a photoinitiator capable of causing or initiating the polymerization of the elastomer when exposed to appropriate actinic light. The compositions, as already indicated, are preferably flowable, deformable and substantially free of any shape memory prior to activation by actinic light so that the composition can be formed to the dental, including the adjacent soft tissue, surfaces of the oral cavity. The preferred composition assumes a permanent elastomeric remembered form, in response to actinic light exposure. By permanent elastomeric remembered form, it is meant that the dental impression material can be stripped from the teeth or soft tissue by stretching and deforming in response to pressure applied by, in the usual usage, the human hand to pull the material from the teeth or soft tissue while retaining the remembered shape of the teeth in detail to which the material returns upon release of the pressure.

The dental impression material or composition in the usual situation is preferably non-adhering to tooth enamel, amalgam, composite tooth fillings, metal bridgework, and other substances commonly found in a variety of different patients so that the composition can have relatively universal use. The composition should have the non-adhering ready release characteristic when, or after, it is changed from its flowable to its remembered form by exposure to actinic light. The composition should also not harm soft tissue structure in the mouth of the patient, be substantially non-toxic in use, and not induce allergic reactions of substance in the patient population as a whole. The composition should be easily removed from the soft tissue and accurately record the soft tissue shape in permanent elastomeric remembered form.

The dental impression material composition of the present invention is preferably substantially stable against assuming a permanent remembered form when stored actinic light free. The composition is preferably stable when stored as a single one-component material for a long period of time actinic light free, preferably being stable for at least one month, more preferably three months, and most preferably for six months or more. By one-component, it is meant that the dental impression material can be stored in the exact form that it will be used by the dentist so that he preferably does not need to do anything other than mold the composition to the surface (surfaces) that is to have its impression made.

The preferred materials of the present invention have special applications in dentistry in addition to their most preferred application in preparing dental impressions. By dental impressions it is meant, reverse images of dental features in the mouth to serve as molds from which dental prosthesis can be prepared or models for preparing dental prosthesis can be prepared. The preferred materials of the present invention also have application in methods of directly preparing dental prothesis by which term it is meant to include parts of dental prosthesis. This provides the format for an entirely new method of preparing dental prosthesis. A particularly preferred aspect of the present invention is the preparing of dental prosthesis by relining of dentures that are either damaged or no longer fit properly and/or comfortably. For this purpose a thin coating of the material, which shall be called a dental prosthesis material or composition, is applied to the denture and the denture is pressed against the soft tissue of the patient's mouth where it is intended to be seated. Then the thus conformed and shaped prosthesis material is removed in its retained position on the denture and cured to form the reline prosthesis of the denture. If on reinsertion every-thing is not as desired, adjustment can be easily made by stripping off the reline prosthesis or cutting out a portion of it and repeating the forming process directly to the soft tissue as described.

Turning now to consideration of the more preferred classes of actinic light activated compositions for carrying out the invention, the flowable composition that is substantially free of any shape memory is preferably a mixture of one or more polymerizable monomers, oligomers and/or polymers of high or low molecular weight and a photoinitiator capable of causing or bringing about polymerization of the polymerizable material to form an elastomer when exposed to appropriate actinic light.

The presently most preferred composition is characterized by its inclusion of a compound that has at least two ethylenic, especially acryl, unsaturated pendant groups that polymerize through free radical reaction. By acryl it is meant any acrylic pendant groups including especially, but without limitation, those of R in general Formula 1 below.

The present invention is believed, in one of its important aspects, to offer the first truly suitable actinic light activatable polysiloxane composition. In the past, such suitable polysiloxane compounds that had no readily activated cross-linking sites except pendent C-C-double bonds and that would cross-link in response to activation of an actinic light activated initiator were unknown. For example, polysiloxane compounds having sites that can undergo condensation reaction in response to ambient moisture are generally unsatisfactory because they add an additional element of instability in addition to the light instability built into the preferred compositions of the present invention. By the present invention a polysiloxane composition is provided that in preferred aspects contains at least 20%, more preferably 50% and most preferably 80% polysiloxane compound, exclusive of filler. The polysiloxane compound ingredient in this sense can be made up all of one compound having a single molecular structure or of compound, meaning compounds, of differing molecular structure. The siloxane compositions may contain substantial amount of fillers as thickeners and to otherwise modify their physical properties. The initiator for cross-linking the polysiloxane compound when activated by actinic light may be a single compound or a system containing a number of compounds. By polysiloxane it is meant a compound (molecule) having within the molecular structure a silicon oxygen linkage in a repeating form of at least 2.

Compounds suitable for use in a broader sense in the present invention have a general formula in their preferred embodiments as follows:

FORMULA 1
$$R-A_x-B_y-R$$

x = O to n
y = O to n

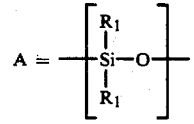

R = 1a, 2a, 3a

FORMULA 1

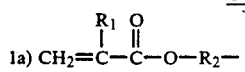

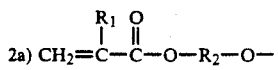

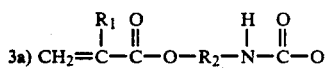

R (The R1 = H, alkyl, sub alkyl, F, CN, aryl, sub aryl, term sub as used in this application means substituted, as or example, sub alkyl.) R2 = alkylene, sub alkylene, arylene, sub arylene. B = Any organic radical substituent such, by way of example, as alkylene, sub alkylene, arylene, sub arylene, urethane, ester, sulphone, oxyalkylene, sub oxyalkylene and substituted substituents thereof. n = 1 or more R, R1, R2 B and n can be the same or different. It being further understood that the backbone of the compound of the general formula may be a homopolymer of B and alternate block or random block copolymer of A Preferably the compound of the general formula has no readily reactive or cross-linking sites except pendent C-C double bonds.

The presently more preferred composition is a mixture of polyorganosiloxanes containing at least two acryl groups, preferably at least two methacryl. The most preferred composition contains a first polyorganosiloxane containing not more than 3 polymerizable or acryl groups, and a second polyorganosiloxane containing at least 3 such acryl groups, and most preferably no more than 20 silicon atoms per molecule. Preferably the first polyorganosiloxane contains 2 acryl groups, more preferably at least 2 methacryl groups. Depending on the number of such polymerizable groups per molecule, the molecular weight of the polyorganosiloxanes themselves, and the organo substituents upon them, materials with varying degrees of hardness, shrinkage upon polymerization, and hydrophobicity may be exhibited by the impression material. In one preferred embodiment polyorganosiloxanes containing one acryl group are used as preferred plasticizers. Preferably the acryl group is a methacryl group in the plastis:zer also.

In the more preferred polyorganosiloxane compounds, referring to the general formula above y is 0 and x for the first polyorgansiloxane is 2 to 20,000, more preferably 4 to 50 and for the second polyorganosiloxane 2 to 10,000, more preferably 2 to 20. Preferably at least 50% of the radicals $R_1$ are monovalent hydrocarbon radicals, preferably methyl radicals, and examples of other suitable radicals are, ethyl, phenyl, and 3,3,3-trifluoropropyl radicals. Exemplary of the preferred siloxanes would be compounds wherein n is an integer selected so that the viscosity of the prepolymer at 25° C. is from 10 to 1,000,000 cps measured with Brookfield viscometer, preferably not more than 300,000 cps. Usually n is from 10 to 2,000.

The more preferred polyorganosiloxanes are those having the following formulas:

FORMULA 2

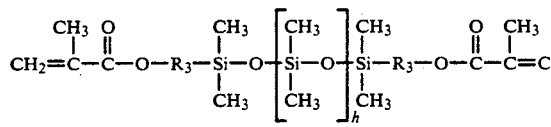

$R_3$ = a saturated alkylene, sub alkylene, aryl, sub arylene.

$R_3$ may be the same or different.

h = 1 to n.

FORMULA 3

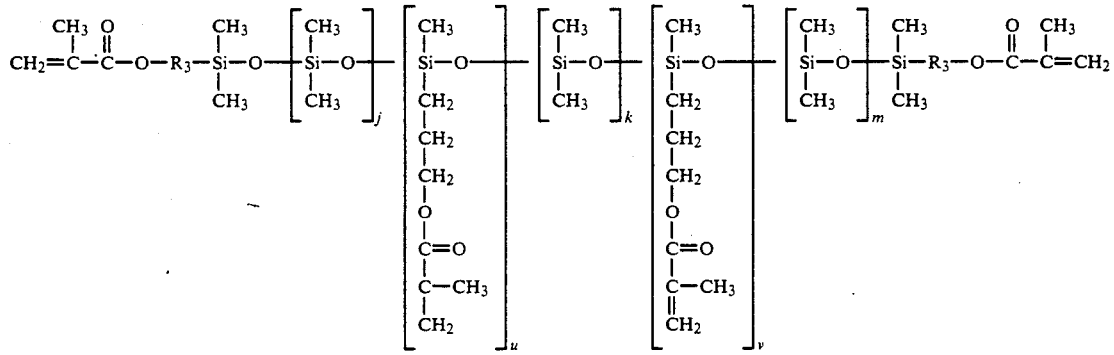

j and m = 1 to n
K = 0 to n
u = 1 to n
v = 0 to n

Siloxane radicals with u, k and v exponents can repeat, alternately forming multiple blocks, the blocks can be the same or different powers of u, k and v.

If a siloxane contains more than two (meth) acryl groups per molecule, it may be regarded as providing a site for active cross-linking and clustering of the prepolymers, when used in minor proportions in order to alter the elastic properties of the polymerized mass.

Because the polyorganosiloxane polymer that is the preferred compound for use in the dental impression material composition of the present invention is also an independent aspect of the present invention it is pointed out that the polyorganosiloxane polymer can be applied to the preparation of self curing dental impression materials by using the known curing systems for such impression materials, such as, a catalyst paste containing as the initiator, benzoyl peroxide, with fillers such as quartz, talc and silica, a diluent such as a (substituted) polydimethyl siloxane with a molecular weight, for example, of 4,000 and a stabilizer such as BHT (butalated hydroxy toluene). The base paste would correspondingly contain an accelerator such as dihydroxyethyparatoluidine, a diluent such as a polydimethylsiloxane and fillers. By "self curing" it is meant a dental impression paste composition consisting of such pastes that, when combined, will polymerize at a predetermined rate due to the additional polymerization induced by reaction of the peroxide and amine rather than actinic light.

Examples of other embodiments of the general Formula 1 when x=o, would be polymerizable oligomers or polymers containing ethylenic allyl unsaturated terminal groups, such as methacryloxy or acryloxy, which, for example, could be the reaction product of one mole polypropylene glycol and two moles 1,6 hexamethylene diisocyanate, which is then reacted with two moles of 2-hydroxyethyl methacrylate (HEMA). Thus, a polyether backbone $B_y$, might be employed in the manner of the silicon of Formula 2. Preferably y is from 2 to 2,000, more preferably 10 to 100. Exemplary of the backbones of Formula 1 when x=o would be polyester, polysulfone, polyaryloxy, polyethylene, polyarylene, polyisocyanates and polyamides, their block and random block copolymers. Likewise should x be 1 or more in general Formula 1, the range of useful backbone structures would include the classes above, singly or in combination as copolymers with substituted polysiloxane unities described in the general formula, FORMULA I, as ($A_x$).

In preferred block copolymers x and y are both preferably from 1 to 1,000 more preferably 2 to 100 and A and B preferably would each repeat 1 to 50 times more preferably 1 to 10 times and may be the same or different both within the block and block to block.

In one more preferred embodiment of the present invention the dental impression composition is a combination including the preferred organosiloxanes and one or more of the preferred non-siloxane hydrocarbyl groups. The siloxane would be present in a quantity sufficient to attain the desired physical properties (especially hydrophobicity, release characteristics and viscosity control, hardness, and dimensional stability). The amount of siloxane compounds could vary broadly, conceivably from only 1% or 2% to up to 99%, but more preferably from 5% to 99% and in the most preferred filed dental impression composition about 10 to 75% with the balance being made up with organic filler, other lymeric compounds and small quantities of initiators, stabilizers and the like.

The photoinitiating system may be one of many known in the art to promote polymerization of the unsaturated acryl groups of the elastomer used, when activated by actinic light of the appropriate wavelengths, strength and length of exposure time. Such systems include, but are not limited to camphoroquinone and other alpha-beta diketones, alone or with reducing agents, such as secondary and tertiary amines, sulfinates, and the like.

The amount of photopolymerization sensitizers and accelerators and their type are selected with due consideration to the intensity of the light source and the activating wavelength(s) and their own capacity to initiate polymerization. Sensitizers for use with organopolysiloxanes, for example camphoroquinone, may be typically used in concentrations between 0.05 and 5% by weight of the acryl compounds which are preferably organopolysiloxane, most preferably between 0.01 and 1.0%. Photopolymerization accelerators, for example, tertiary amines, including, for example, methyldiethanolamine, diethanolamine, or triethanolamine may be used. These are preferably used in amounts of between 0.1 and 10% of the concentration of the acryl compounds which are preferably polyorganosiloxanes, but most preferably between 0.1 and 5%.

The impression material can be a viscous liquid, or it can be modified with fillers to result in more viscous pastes or even putties. The fillers used should have suitable optical characteristics so as not to interfere with the transmission of actinic light through the material in order to initiate the photoinitiator system. The filler particles should have size and surface area appropriate to effect the desired viscosity change.

Reinforcing fillers may also be used in the composition of the present invention. Preferred reinforcing fillers have a surface area of at least 50 square meters per gram and are exemplified by pyrogenically-produced silicon dioxide, silicic acid hydrogels dehydrated so as to maintain their structure, silicon dioxide Aerogels, and precipitated silicon dioxide. Other fillers may be used which are considered to be non-reinforcing fillers. Such fillers are generally those having a surface area less than 50 meters per square gram, and include calcium carbonate, fused quartz powder, powdered calcium silico aluminate, titanium dioxide, zirconium silicate, aluminum silicate, etc. These materials may be ground or formed by a variety of means to provide particulate powdered filler of sizes between 0.001 and 100 microns, depending on the application. Particles of individual average sizes of 0.01 and 40 microns are especially preferred.

All of these fillers, but especially the reinforcing fillers, can have organosilyl groups on their surface if they have been pretreated, for example, with dimethylhalogen silanes, or if they have been manufactured, for example, by reaction of aqueous silica sol with organo halogensilanes, or have been rendered hydrophobic in some other way. Mixtures of different fillers can be used. The fillers can be used in amounts of from 1% to 120% by weight, especially from 5% to 100% weight, relative to the other components. Non-reinforcing fillers may be used at concentrations of at least 20% by weight relative to the prepolymers present, whereas reinforcing fillers may be appropriately used in the compound at from 1% to 80% by weight, relative to the total weight of all prepolymers present. An important consideration is that the amount and the type of filler is so selected that actinic irradiation may pass through the polymerizable mass in order that polymerization can occur upon irradiation to the depth of the impression, but the filler need not match the refractive index of the resins exactly.

If a polysiloxane contains no (meth) acryl groups or only one such polymerizable group per molecule, it may be regarded as a plasticizer. Such plasticizers include, for example, materials of the general formulas set out above as Formula 1 except one of the terminal R groups would be replaced by $R_1$ other than R. Such plasticizers are generally added to alter the hydrophobicity, the softness or hardness of the composition, its viscosity or tackiness, etc. Still other plasticizers may include, for example, phthalates, azelates, glycerides, and other materials known to the art.

Organic resins, for example PVC powder or methacrylate polymer powder, polyethylene and the like, may be used as suitable extenders and plasticizers. The compositions of the invention may be stabilized by the addition of hydroquinone, catechol, and other similar wellknown polymerization inhibitors for the polymerization of (meth) acrylate compounds. Other optional ingredients include pigments and flavoring substances.

The actinic light, except for ambient light, is preferably substantially limited to the visible light spectrum of about 360 to about 600 nanometers, more preferably 400 to 500 nanometers. The composition is substantially stable against assuming a permanent remembered form when stored actinic light free. The composition is non-toxic in use in the oral cavity, is stable in storage for at least one (1) month as a one-component composition when actinic light free, and assumes a permanent elastomeric memory when exposed to light filtered to limited wave lengths within the visible light range for one (1) minute to a depth of one (1) inch.

The one-component composition of the present invention can be packaged in various ways, including being preloaded into a syringe from which the dentist can express the material directly onto the soft or hard tissues to be reproduced. The composition can also be preloaded into a dental impression tray which can be placed by the dentist directly into the mouth of the patient, or can be preloaded into a collapsible tube from which the dentist can squeeze the material into a dental impression tray that passes actinic light prior to placement in the patient's mouth. An important point is for the container or its overwrap to be metal or otherwise opaque to actinic light, or be packaged in such a manner as to protect the composition of the invention from actinic light prior to use by the dentist.

In a preferred embodiment of the present invention the dentist places the special tray filled with the composition of the present invention in the mouth of the patient in such a way that the impression material fully contacts the entire area of the oral tissues of which an impression is being made. An optional step may be taken by the dentist prior to placing the filled tray in the patient's mouth in order to avoid entrapping air bubbles at the tissue surface or in constricted areas, the dentist would coat the surface of the tissues, especially constricted areas, such as between teeth, with a more fluid impression material of the present invention preferably by extrusion from a syringe, and then place the filled tray as described above.

After placement of the special tray, the impression material is now polymerized by visible light within a minute, more preferably within 30 seconds and most preferably within 20 seconds or less, by a source of actinic light, such as a PRISMA-LITE ™ polymerization unit of The L. D. Caulk Company Division of Dentply International Inc., which produces visible light with a band of wavelengths between 400 and 500 nanometers and an energy output of approximately 400 milliwatts per square centimeter from the tip of the unit's light guide. The polymerization time can vary depending on the intensity and wavelength of the light used, the quantity of material to be polymerized, and the tray used. For example, the tray could be a special tray of the construction described below.

The time required for the dentist and the patient to wait for polymerization or setting of the shape to take place may be reduced from 8–10 minutes to one minute or less, and the total time required for placement and curing of the one-component impression material of the present invention may be reduced to 2–3 minutes, as compared to approximately 15 minutes in conventional techniques, which require mixing of two-component impression materials.

The impression tray to be used with the composition of the present invention must be capable of transmitting light to all areas of the impression material that are to be activated directly by the actinic light. One simple construction would be simply a standard transparent plastic tray, whereby polymerizing light can be directed through all portions of the base of the tray onto the material inside the tray.

A newly developed tray that is the subject of a separate patent application filed on the same day as this patent application, is case number 1533, assigned to the same assignee as the present patent application. This tray has a light guide means, such as a short solid light pipe rod at the anterior portion of a transparent tray which transmits light from the light source into the tray. The light is then transmitted to the impression material by the body of the tray itself. The light may be reflected or deflected directly into the material by a reflective tray surface. Such reflective surfaces are provided by metallized mirror-like coatings on the outer tray surface, or by geometric shaped facets, grooves or ridges which reflect or deflect light at roughly 90° from the general surface of the tray. The facets, grooves or ridges occur either on the outer or inner tray surfaces.

The impression tray could be prefilled with impression material and be wrapped entirely with a metal foil-plastic laminate material to be opened at an area allowing for the taking of the impression only at the time of use, which would prevent the impression material from being exposed to light before use. The metal foil could serve the dual function of preventing unintentional light exposure and subsequently providing a reflecting surface for the light supplied to the tray to bring about polymerization.

In another preferred embodiment of the present invention the dentist would prepare a dental prosthetic by taking a removable denture that is no longer fitting comfortably in a patient's mouth and apply to all of the areas of the denture that contact the patient's soft tissue, a thin coating of one of the compositions of the present invention. The dentist would then reinsert the denture, into the patient's mouth and engage the composition while it is flowable and at least substantially free of memory with the surfaces in the oral cavity that are to be reproduced as the new closely fitting negative dental prosthetic part to the surface. The denture is pushed firmly into place, forcing the composition against the patient's dental surface until some of the composition flows into good conformity with the surface to form the composition into an accurate negative impression of the oral surface. The denture is then removed from the patient's mouth and inserted into a TRIAD ™ light curing unit (a product of Dentsply International Inc.) and actinic light is impinged on the negative impression formed composition by operation of the unit. This photopolymerizes the composition to a degree that the composition assumes a permanent elastomeric remembered form of the negative of the oral surface. It will be understood that the flowable composition is carried on the surface of the removable denture that is to be juxtaposed against the soft tissue in the oral cavity when the composition is forced toward the soft tissue surface.

Functional reline materials are inserted, for example, in existing dentures and are worn by the patient, in function as it were, for from a few minutes to 24 hours or more, during which time an impression of the self-positioning and functioning denture is more accurately registered. These compositions, soft, elastic and conforming to the tissues, are a treatment for abused and irritated mucosa caused by the ill-fitting denture, and are worn from periods of days, months or years.

The invention is further illustrated by the following examples:

EXAMPLE 1

A silicone dimethacrylate was prepared according to the following formulation:

| | |
|---|---|
| Polydimethylsiloxane - hydroxy terminated (PS341, a product of Petrarch Inc.) | 85% |
| Gamma-Methacryloxypropyltrimethoxysilane (Silane A-174, a product of Union Carbide) | 5.0 g. |
| Dibutyl tin dilaurate | 0.18 g. |

The procedure for preparing the silicon dimethacrylate was as follows:

The siloxane was charged into a 3 neck round bottom flask equipped with a magnetic stirrer thermometer and a small finger condenser. The silane and dibutyl tin dilaurate were mixed and charged into a separatory funnel. Nitrogen was passed through the flask during the reaction. The flask was initially cooled with an ice bath and the addition of the silane-catalyst mixture was begun. After all was added the mixture was heated with an oil bath to 157° C., which took about one hour. The oil bath was removed and the contents were allowed to cool with stirring.

The viscosity of the prepolymer resin, Product 1, at 22° C. using a Brookfield viscometer was 380 cps.

The resin, Product 1, was then formed into a visible light curing composition by hand in a beaker at ambient conditions.

| | |
|---|---|
| Product 1 | 94.74 parts by wt. |
| Camphoroquinone | 3.78 parts by wt. |
| Saccharin | 9.48 parts by wt. |
| Di-t-butyl peroxide | 0.95 parts by wt. |

The composition was then tested by exposure to the PRISMA LITE® dental light (product of the LD Caulk Div. of Dentsply International Inc.). The composition cured to a soft elastic solid state after a one minute exposure.

EXAMPLE 2

A suitable elastomeric prepolymer was prepared by reacting 1 mol of polypropylene glycol (Union Carbide NIAX PPG-2025) and 2 mols of 1,6 hexamethylene diisocyanate, with 0.05% dibutyl tin dilaurate as a catalyst. The reaction was carried out using a standard glass reactor at ambient conditions. This prepolymer then was further reacted in the reaction vessel at ambient conditions with a slight excess of 2-hydroxyethyl methacrylate (ratio 1:2.1). The reaction product (hereinafter referred to as Product 2) was a viscous liquid at room temperature.

The dental impression forming composition was then compounded in the same manner as in Example 1 at ambient conditions.

| | |
|---|---|
| Product 2 | 100 parts by wt. |
| Camphoroquinone | 0.15 parts by wt. |
| p-dimethylamino benzaldehyde | 0.5 parts by wt. |

The dental impression forming composition was then tested for its relevant characteristics and the results are recorded in table 1 below.

A dental impression was also formed by placing or loading the dental impression forming composition in a clear plastic dental impression tray. The loaded tray was then pressed on a stone model and irradiated with light from a 150 watt tungston-halogen lamp for one minute.

The tray with the now cured elastomeric dental impression composition was then separated from the teeth and adjacent tissue in conventional manner of dentistry and by visual observation with the unaided eye found to be of excellent quality having no visible porosity.

EXAMPLE 3

The procedure of Example 2 was repeated except as designated below.

| | |
|---|---|
| Product 2 | 100 parts by wt. |
| Bis(methacryloxy propyl) tetramethyl disiloxane (Petrarch Systems Inc.) | 10 parts by wt. |
| Camphoroquinone | 0.115 parts by wt. |
| p-dimethylamino benzaldehyde | 0.5 parts by wt. |

The dental impression forming composition was then tested for its relevant characteristics and the results are recorded in table 1 below. A dental impression was also formed as described in Example 2 and found to have a smooth surface with no visible porosity as determined by visual inspection with the unaided eye.

EXAMPLE 4

The procedure of Example 2 was repeated except as designated below.

| | |
|---|---|
| Product 2 | 100 parts by wt. |
| Bis(methacryloxy propyl) tetra methyldisiloxane | 10 parts by wt. |
| Camphoroquinone | 0.115 parts by wt. |
| Methyl diethanol amine | 0.5 parts by wt. |

The dental impression forming composition was then tested for its relevant characteristics and the results are recorded in table 1 below. A dental impression was also formed as described in Example 2 and found to have the following characteristics as determined by visual inspection with the unaided eye to have a smooth surface without visible porosity.

TABLE 1

| Example | Shore A Hardness* | % Negative Dimensional Change (ADA Spec. 19) | % Compression Set (ADA Spec 19)** | % Strain (ADA Spec 19) |
|---|---|---|---|---|
| 2 | 64 | 0.55 | 0.35 | 1.60 |
| 3 | 50 | 0.60 | 0.35 | 1.55 |
| 4 | 51 | 0.40 | 0.45 | 2.75 |

*Shore A hardness was determined using ASTM dated 1975.
**ADA Spec 19 is Specification 19 of the American Dental Association dated April, 1978.

As illustrated in Table 1, following radiation exposure for 20 seconds in the 400–500 nanometer wavelength band with an energy output of approximately 400 milliwatts per square centimeter, the softness/hardness of the elastomer (Shore A) measured only 51 in Example 4, versus 64 in Example 2. This illustrates the effect of the disiloxane.

A property considered critical by American Dental Association Standard 19 for elastomeric impression materials, is strain (or deflection under load) where specification limits are imposed from 2.0 to 20.0%. The above modified resins of Example 4 passed this test at 2.75%, whereas the elastomer without disiloxane and methyl diethanol amine at 1.6%, Example 2, did not.

Furthermore, the siloxane modifications accomplish these valuable changes without significantly affecting other critical properties of the impression material, such as dimensional change, and elastic recovery after being stressed in compression.

EXAMPLE 5

An elastomeric prepolymer was prepared according to the following formulation:

| | |
|---|---|
| Polypropylene glycol with a molecular weight of 4600 (Pluracol 628, BASF Wyandotte Corporation) | 967.5 g |
| Isocyanatoethyl methacrylate (Developmental Monomer XAS-10743.00, Dow Chemical) | 65.5 g |
| Dibutyltin dilaurate | 0.5165 g |

The procedure was as follows:

One mole of polypropylene glycol (2 equivalents of hydroxy) are reacted with two moles of isocyanatoethyl methacrylate (2 equivalents of isocyanate) employing 0.05% dibutyl tin dilaurate.

The polypropylene glycol was dewatered with molecular sieve (4A) for two days. Then it was charged into a 2 liter reactor. Stirring and dry air flow through the reactor was begun. The dibutyl tin dilaurate was added to the glycol dropwise and allowed to stir in. Then the isocyanatoethyl methacrylate was added to the glycol-catalyst mixture dropwise using a separatory funnel. The addition was done at room temperature and the drop rate was kept around 10 drops every 20 seconds in order to keep from having too much exotherm. After approximately two and a half hours, all the isocyanatoethyl methacrylate had been added and the pot temperature was 27.5° C. The mixture stirred at this temperature for two hours. Then a heating mantle was put around the reactor and the mixture was heated to 50° C. where it was kept for 16 hours. At this point the heating mantle was removed and the mixture was allowed to stir at room temperature for another 24 hours. The pot contents were sampled and it appeared from titration that all the isocyanatoethyl methacrylate had reacted. The prepolymer will hereafter be referred to as Product 3.

The viscosity of the prepolymer resin, Product 3 was 1550 cps at 25° C. using a Brookfield viscosimeter:

The dental impression forming composition was then compounded as in Example 1 at ambient conditions.

| | |
|---|---|
| Product 3 | 100 parts by wt. |
| Camphoroquinone | 0.15 parts by wt. |
| Methyl diethanol amine (MDEA) | 0.5 parts by wt. |

The dental impression forming composition was then tested for its relevant characteristics with the following results:

Upon irradiation with visible light, the material cured to an elastic solid with a shore A hardness of about 40 (4'30" cure) when tested according to ADA specification 19 (1984) for non-aqueous impression materials. The resin was further tested according to ASTM Method (1975) for non-aqueous impression materials and gave a 0.60% compression set and 7.9% strain for the same cure time and to have a dimensional change of ±0.07% one hour after cure when tested according to ADA Specification 19.

By the present invention, for the first time, a practical dental impression material will be commerically feasible that can be prepared as a one-component composition that can be delivered to a dentist, stored until needed and then directly used without a requirement of premixing two materials shortly before use. This new material is very safe to use because its curing is initiated by contacting the material with actinic light within the visible light spectrum. The dentst's freedom to work with the material for the time required to obtain the best positioning of the dental impression material and then quickly bring about a cure without a long period of waiting for completion of the setting or curing of the impression material is provided. And as another feature, an entirely new silicon polymer composition is provided for use as a visible light cure dental impression material. The new silicon polymer composition is also adaptable to a functional dental reline material, and as a direct or indirect reline and treatment material for dentures.

While in accordance with the patent statutes, what is considered to be the preferred embodiment of the invention has been described, it will be obvious to those skilled in the art that numerous changes and modifications may be made therein without departing from the invention and it is therefore aimed in the appended claims to cover all such equivalent variations as fall within the true spirit and scope of the invention.

It is claimed:

1. A method of forming a dental impression in the oral cavity comprising
   (a) engaging composition that is flowable and at least substantially free of memory with a surface in the oral cavity that is to have its dental impression taken, including forcing a tray of said composition toward the surface until some of said composition flows to assure good engagement of said composition with the surface; and
   (b) maintaining said tray in contact with said composition and passing actinic light through at least an integral part of said tray photopolymerizing said composition to a degree that said composition assumes a permanent elastomeric remembered form.

2. The method of claim 1 wherein said actinic light, except for ambient light, is substantially limited to the visible light spectrum of about 360 to about 600 nanometers.

3. The method of claim 1 wherein said tray passes actinic light through the majority of its mass to said composition.

4. The method of claim 1 wherein said composition is substantially stable against assuming a permanent remembered form when stored actinic light free.

5. The method of claim 1 wherein said composition is substantially non-absorbing to tooth enamel when changed from said flowable to said remembered form by exposure to actinic light and in said remembered form being deformable in response to pressure applied by the human hand to pull of of teeth retaining the remembered shape of the teeth in detail.

6. The method of claim 1 wherein said composition is non-toxic in use in the oral cavity, is stable in storage for at least one (1) month as a one-component composition when actinic light free, and assumes a permanent elastomeric memory when exposed to light filtered to limited wavelengths within the visible light range for one (1) minute to a depth of one (1) inch.

7. The method of claim 1 wherein said composition comprises a polysiloxane.

8. The method of claim 7 wherein said composition is photopolymerized at least in part through photo-crosslinking of two pendent C-C-double bonds.

9. The method of claim 8 wherein said polysiloxane comprises organosiloxane with two pendent C-C-double bonds prior to photopolymerizing and said composition prior to said photopolymerizing is substantially free of sites for condensation polymerization.

10. The method of forming a dental impression of claim 11 wherein said composition comprises a compound that has at least two acryl ethylenic unsaturated pendant groups that polymerize through free radical reaction, said compound having the general formula $$R-A_x-B_y-R$$

x = 0 to n
y = 0 to n

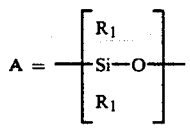

R = 1a, 2a, 3a

1a) 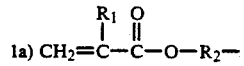

2a) 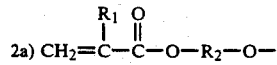

3a) 

$R_1$ = H, alkyl, sub alkyl, F, CN, aryl, sub aryl
$R_2$ = alkylene, sub alkylene, arylene, sub arylene
B = An organic radical substituent;
n = 1 or more; and it being further understood that the backbone of the compound of the general formula may be a homopolymer of A or B or an alternate block or random block copolymer of A or B and A and/or B may be the same or different for each n within the compound.

11. The method of claim 10 wherein said dental impression composition includes at least two polyorganosiloxane compounds, a first polyorganosiloxane containing not more than 3 polymerizable acryl groups, and a second polyorganosiloxane containing at least 3 acryl groups.

12. The method of claim 11 wherein y is 0 and said first and said second polyorganosiloxanes are according to said general formula and x, for the first polyorganosiloxane is 2 to 20,000 and for the second polyorganosiloxane 2 to 10,000.

13. The method of claim 12 wherein said dental impression composition includes at least about 20% by weight, exclusive of filler, of compounds according to said general formula and at least about one half of said 20% is of compounds wherein y=o and said first polyorganosiloxane has the formula

FORMULA 2

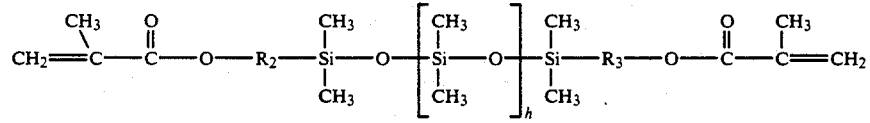

$R_3$ = saturated alkylene, sub alkylene, ary, sub arylene
$R_3$ may be the same or different
h = 1 to n and said second polyorganosiloxane has the formula

FORMULA 3

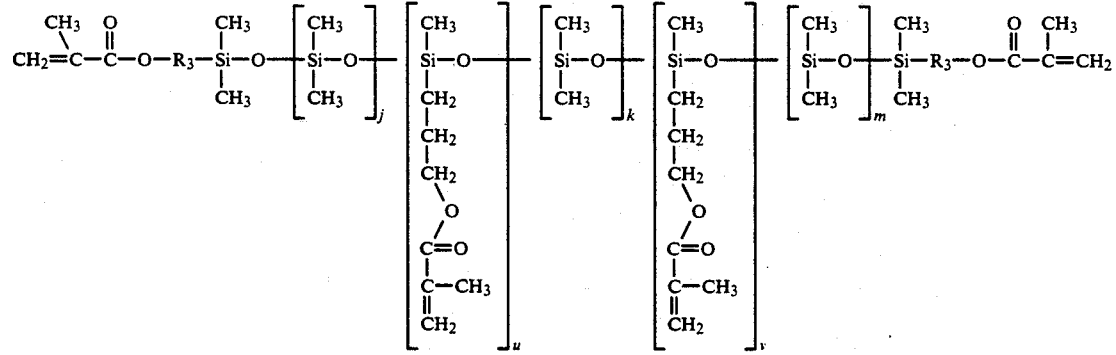

j and m = 1 to n
k = o to n
u = 1 to n
v = o to n

Siloxane radicals with u, k and v exponents can repeat, alternately forming multiple blocks, the blocks can be the same or different powers of u, k and v.

* * * * *